United States Patent [19]

Satake

[11] Patent Number: 5,741,797
[45] Date of Patent: Apr. 21, 1998

[54] HETEROATOM SUBSTITUTED ALKYL BENZYLAMINOQUINUCLIDINES

[75] Inventor: Kunio Satake, Handa, Japan

[73] Assignee: Pfizer Inc., New York, N.Y.

[21] Appl. No.: 556,916

[22] PCT Filed: May 13, 1994

[86] PCT No.: PCT/JP94/00781

§ 371 Date: Nov. 20, 1995

§ 102(e) Date: Nov. 20, 1995

[87] PCT Pub. No.: WO94/26740

PCT Pub. Date: Nov. 24, 1994

[30] Foreign Application Priority Data

May 19, 1993 [JP] Japan ................ 5/117102

[51] Int. Cl.⁶ ............ C07D 403/02; C07D 453/02; A61K 31/435
[52] U.S. Cl. .................... 514/305; 546/133
[58] Field of Search ................. 546/133; 514/305

[56] References Cited

U.S. PATENT DOCUMENTS 5,294,744  3/1994  Godek et al. ............ 568/442

FOREIGN PATENT DOCUMENTS 9220676  11/1992  Japan .
9221677  12/1992  Japan .
9319064  9/1993  Japan .

Primary Examiner—Matthew V. Grumbling
Attorney, Agent, or Firm—Peter C. Richardson; Paul H. Ginsburg; B. Timothy Creagan

[57] ABSTRACT

Compounds useful in the treatment of inflammatory disorders, central nervous system disorders and other disorders of the formula I and the pharmaceutically-acceptable salts thereof;

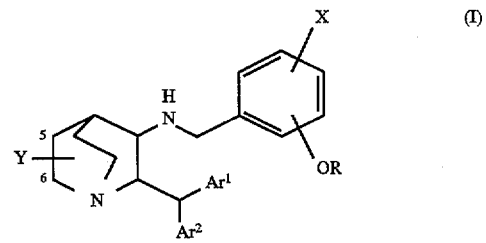

wherein R is $C_1$–$C_6$ alkyl; X is $C_1$–$C_6$ alkyl having one or more substituents which include at least one heteroatom; $Ar^1$ and $Ar^2$ are each, independently, aryl optionally substituted by one $C_1$–$C_6$ alkyl, $C_1$–$C_6$ alkoxy, $C_1$–$C_6$ alkylthio, halogen, cyano, nitro, phenoxy, mono $C_1$–$C_6$ alkylamino, di $C_1$–$C_6$ alkylamino, halosubstituted $C_1$–$C_6$ alkyl, or halosubstituted $C_1$–$C_6$ alkoxy; Y is hydrogen, $C_1$–$C_6$ alkyl, $C_2$–$C_6$ alkenyl, $C_3$–$C_8$ cycloalkyl, Z—$(CH_2)_p$—, or W—$(CH_2)_m$—$CHR^2$—$(CH_2)_n$—$NR^1CO$— wherein Y is at the 4-, 5- or 6-position on the quinuclidine ring; $R^1$ is hydrogen, $C_1$–$C_6$ alkyl, benzyl or —$(CH_2)_r$—W; $R^2$ is hydrogen or $C_1$–$C_6$ alkyl which may be substituted by one hydroxy, amino, methylthio, methylmercapto, benzyl, 4-hydroxybenzyl, 3-indolylmethyl or —$(CH_2)_r$—W; $R^1$ may form a ring with $R^2$; Z is $C_1$–$C_6$ alkoxy, —$CONR^4R^5$, —$CO_2R^4$, —$CHR^4OR^5$, —$CHR^4NR^5R^6$, —$COR^4$, —$CONR^4OR^5$ or optionally substituted aryl; each W is independently cyano, hydroxymethyl, $C_2$–$C_6$ alkoxymethyl, aminomethyl, mono $C_1$–$C_6$ alkylaminomethyl, di $C_1$–$C_6$ alkylaminomethyl, carboxyl, carbamoyl or $C_1$–$C_6$ alkoxycarbonyl; $R^4$, $R^5$ and $R^6$ are independently hydrogen, $C_1$–$C_6$ alkyl, $C_1$–$C_6$ alkoxy, $C_3$–$C_8$ cycloalkyl or an optionally substituted aryl or heterocyclic group; p is 0 to 6; and m, n and r are each, independently, 0 to 3.

7 Claims, No Drawings

1

HETEROATOM SUBSTITUTED ALKYL BENZYLAMINOQUINUCLIDINES

This is a 371 of PCT/JP94/00781, filed May 13, 1994.

TECHNICAL FIELD

This invention relates to novel and useful substituted alkyl benzylaminoquinuclidine compounds of interest to those in the field of medical chemistry and chemotherapy. More particularly, it is concerned with a novel series of heteroatom substituted alkyl benzylaminoquinuclidines, including the pharmaceutically acceptable salts and pharmaceutical composition thereof, which are of special value in view of their ability to antagonize substance P. In this way, these compounds are of use in treating gastrointestinal disorders, central nervous system disorders, inflammatory diseases, asthma and pain, migraine or emesis in mammalia. The invention also includes a new method of therapy within its scope.

BACKGROUND ART

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *J. Med. Chem.*, 25, 1009 (1982)), as well as in central nervous system disorders such as anxiety and schizophrenia, in respiratory and inflammatory diseases such as asthma and rheumatoid arthritis, and in gastrointestinal disorders and diseases of GI tract, such as ulcerative colitis and Crohn's diseases (see D. Regoli in "*Trends in Cluster Headache*" edited by F. Sicuteri et al., Elsevier Scientific Publishers, Amsterdam, 1987, PP. 85–95).

It is recently reported that substance P antagonists are effective for treatment of emesis (EP 0533280 A). In addition the relationship between substance P and sunburn has been discussed.

In the recent past, some attempts have been made to provide peptide-like substances that are antagonists for substance P and other tachykinin peptides in order to more effectively treat the various disorders and diseases listed above. The peptide-like nature of such substances make them too labile from a metabolic point of view to serve as practical therapeutic agents in the treatment of disease. The non-peptidic antagonists of the present invention, on the other hand, do not possess this draw back, being far more stable from a metabolic point of view.

Among the prior art relating to compounds of similar structure and similar pharmacological activity to the object compounds of the present invention, there are WO 90/05729, WO 92/20676 and JP application No. 307179/92. WO 90/05729 discloses a series of cis-3-[(cyclic) methylamino]-2-[(α-substituted)arylmethyl] quinuclidines including 2-benzhydryl derivatives, 2-substituted benzhydryl derivatives (wherein the substituents are alkyl, alkoxy, halogen and the like), 2-(bis-(2-thienyl)methyl) derivatives and the like. In WO 92/20676 a series of 3-[2-methoxy-5-(substituted) benzylamino]-2-benzhydrylquinuclidine compounds, which include 4-alkenyl derivatives, 6-phenethyl derivatives, 5- and 6-dialkylaminocarbonyl derivatives, 5-dialkylaminoalkyl derivatives, 5- and 6-hydroxyalkyl derivatives, 5-alkylaminocarbonyl derivatives, 5-aminocarbonyl derivatives, 5- and 6-carboxyl derivatives, 5- and 6-alkoxycarbonyl derivatives, 5-(N-alkoxy-N-alkyl)aminocarbonyl derivatives and 5-morpholinocarbonyl derivatives and the like, are disclosed. Additionally, the compounds disclosed in that patent application have various kind of substituents also at 5-position on the benzene ring in benzylamino moiety, i.e. alkoxy such as methoxy, alkyl such as isopropyl, alkylthio such as methylthio, halosubstituted alkoxy such as trifluoromethoxy, halogen, alkylsulfinyl such as methylsulfinyl, dialkylamino such as dimethylamino and the like. JP application No. 307179/92 discloses peptidic 3-aminoquinuclidine derivatives having amido side chain on the quinuclidine ring.

The compounds disclosed in WO 90/05729, WO 92/20676 and JP application No. 307179/92 have activity as substance P antagonists, anti-inflammatory activity and antipsychotic activity.

Furthermore, when N-(5-(1-methylethyl)-2-methoxyphenyl)methylamino-2-diphenylmethyl-1-azabicyclo[2.2.2]octan-3-amine (a compound disclosed and claimed in WO 92/21677) was incubated with homogenized rat-liver supernatant, small amounts of the compound of formula I of this invention, wherein $Ar^1$ and $Ar^2$ are each phenyl, Y is hydrogen, OR is 2-methoxy and X is 5-(1-hydroxy-1-methylethyl), and the compound of formula I of this invention, wherein $Ar^1$ and $Ar^2$ are each phenyl, Y is hydrogen, OR is 2-methoxy and X is 5-(1-methoxy-1-methyethyl), were detected.

BRIEF DISCLOSURE OF THE INVENTION

The inventors made a effort in order to create compounds with substance P antagonistic activity. As a result, they discovered that the novel heteroatom substituted alkyl benzylaminoquinuclidines which are described in the following formula (I) and their pharmaceutically acceptable salts, have excellent activity for the treatment of gastrointestinal disorders, central nervous system disorders, inflammatory diseases, asthma, pain migraine or emesis based on substance P antagonistic activity:

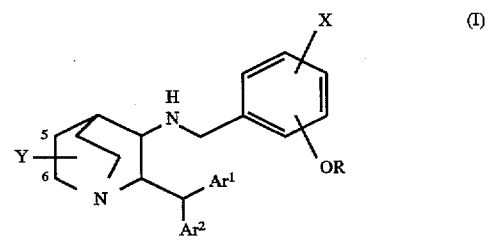

wherein
R is $C_1$–$C_6$ alkyl;
X is $C_1$–$C_6$ alkyl having one or more substituents bonded through a heteroatom;
$Ar^1$ and $Ar^2$ are each, independently, aryl optionally substituted by one $C_1$–$C_6$ alkyl, $C_1$–$C_6$ alkoxy, $C_1$–$C_6$ alkylthio, halogen, cyano, nitro, phenoxy, mono $C_1$–$C_6$ alkylamino, di $C_1$–$C_6$ alkylamino, halosubstituted $C_1$–$C_6$ alkyl, or halosubstituted $C_1$–$C_6$ alkoxy;
Y is hydrogen, $C_1$–$C_6$ alkyl, $C_2$–$C_6$ alkenyl, $C_3$–$C_8$ cycloalkyl, Z—$(CH_2)_p$— or W—$(CH_2)_m$—$CHR^2$—$(CH_2)_n$ —NR$^1$CO—, wherein Y is at the 4-, 5- or 6-position on the quinuclidine ring;

R$^1$ is hydrogen, C$_1$–C$_6$ alkyl, benzyl or —(CH$_2$)$_r$—W;

R$^2$ is hydrogen or C$_1$–C$_6$ alkyl which may be substituted by one hydroxy, amino, methylthio, mercapto, benzyl, 4-hydroxybenzyl, 3-indolylmethyl or —(CH$_2$)$_r$—W;

Z is C$_1$–C$_6$ alkoxy, —CONR$^4$R$^5$, —CO$_2$R$^4$, —CHR$^4$OR$^5$, —CHR$^4$NR$^5$R$^6$, —COR$^4$, —CONR$^4$OR$^5$ or optionally substituted aryl;

each W is independently cyano, hydroxymethyl, C$_2$–C$_6$ alkoxymethyl, aminomethyl, mono C$_1$–C$_6$ alkylaminomethyl, di C$_1$–C$_6$ alkylaminomethyl, carboxyl, carbamoyl or C$_1$–C$_6$ alkoxycarbonyl;

R$^4$, R$^5$ and R$^6$ are independently hydrogen, C$_1$–C$_6$ alkyl, C$_1$–C$_6$ alkoxy, C$_3$–C$_8$ cycloalkyl or an optionally substituted aryl or heterocyclic group;

p is 0 to 6; and m, n and r are each, independently, 0 to 3.

The compounds of formula I show pharmaceutical activity as substance P antagonists. Therefore they are useful for treatment or prevention of a condition selected from the group consisting of inflammatory diseases (e.g, arthritis, psoriasis, asthma and inflammatory bowel disease), anxiety, depression or dysthymic disorders, colitis, psychosis, pain, emesis gastroesophageal reflux disease, allergies such as eczema and rhinitis, chronic obstructive airways disease, hypersensitivity disorders such as poison ivy, vasospastic disease such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human. Accordingly, the present invention includes pharmaceutical compositions for antagonizing mammal's Substance P which comprises a pharmaceutically acceptable carrier or diluent and a compound of formula I or a pharmaceutically acceptable salt thereof. These pharmaceutical compositions are useful for treating or preventing one of the aformentioned conditions, in a mammal, including a human.

The present invention also relates to a method of antagonizing substance P in a mammalian subject, which comprises administering to said subject an effective amount of a compound of formula I; In this way, the compounds of formula I are useful for treating or preventing the aforementioned conditions in a mammal, including a human.

DETAILED DISCLOSURE OF THE INVENTION

In this specification:

The term "alkyl" is used herein to mean straight or branched hydrocarbon chain radicals including, but not limited to, methyl, ethyl, n-propyl, isopropyl, n-butyl, isobutyl, t-butyl, and the like;

The term "alkenyl" is used herein to mean straight or branched hydrocarbon chain radicals having one double bond including, but not limited to, ethenyl, propen-1-yl, propen-2-yl, 2-methyl-1-propenyl, 1- and 2-butenyl and the like;

The term "alkoxy" is used herein to mean —O-alkyl including, but not limited to, methoxy, ethoxy, propoxy, isopropoxy, n-butoxy, isobutoxy, t-butoxy and the like;

The term "alkanoyl" is used herein to mean —CO-alkyl including, but not limited to, methylcarbonyl, ethylcarbonyl, propylcarbonyl, isopropylcarbonyl, n-butylcarbonyl, isobutylcarbonyl, t-butylcarbonyl and the like;

The term "alkanoyloxy" is used herein to mean —O—CO-alkyl including, but not limited to, methylcarbonyloxy, ethylcarbonyloxy, propylcarbonyloxy, isopropylcarbonyloxy, n-butylcarbonyloxy, isobutylcarbonyloxy, t-butylcarbonyloxy and the like;

The term "alkylamino" and "dialkylamino" is used herein to mean —N(R$^7$)R$^8$, wherein R$^7$ is hydrogen or alkyl and R$^8$ is alkyl, including, but not limited to, methylamino, ethylamino, n-propylamino, isopropylamino, n-butylamino, t-butylamino, dimethylamino, diethylamino, ethylmethylamino and the like;

The term "halogen" is used herein to mean radicals derived from the elements fluorine, chlorine, bromine and iodine.

The term "halosubstituted alkyl" is used herein to mean an alkyl radical substituted with one or more halogens including, but not limited to, chloromethyl, trifluoromethyl, 2,2,2-trichloroethyl and the like;

The term "halosubstituted alkoxy" is used herein to mean an alkoxy radical substituted with one or more halogens including, but not limited to, chloromethoxy, trifluoromethoxy, 2,2,2-trichloroethoxy and the like;

The term "alkylthio" is used herein to mean —S-alkyl including, but not limited to, methylthio, ethylthio, n-propylthio, isopropylthio, n-butylthio, isobutylthio, t-butylthio and the like;

The term "heterocyclic groups" is used herein to mean cycloalkyl which has one or more heteroatoms in the ring including, but not limited to, piperidino, morpholino, thiamorpholino, pyrrolidino, piperidino, tetrahydrofuryl, pyrazolidino, piperazinyl and the like; and The term "aryl" is used herein to mean aromatic radicals including, but not limited to, phenyl, naphthyl, pyridyl, quinolyl, thienyl, furyl, oxazolyl, tetrazolyl, thiazolyl, imidazolyl, pyrazolyl and the like which are optionally substituted by alkyl, alkoxy, alkylthio, halogen, cyano, nitro, phenoxy, mono- or dialkylamino and the like.

The term "alkyl having one or more substituents bonded through a heteroatom" is used herein to mean alkyl which has one or more substituent with heteroatom wherein the substituents with heteroatom include, but are not limited to, hydroxy, halogen, C$_1$–C$_6$ alkoxy, C$_2$–C$_6$ alkanoyl, C$_2$–C$_6$ alkanoyloxy, C$_1$–C$_6$ alkylthio, mono C$_1$–C$_6$ alkylamino, di C$_1$–C$_6$ alkylamino, amino, cyano and azido.

The preferred groups for Ar$^1$ and Ar$^2$ are phenyl and phenyl substituted by halogen, especially phenyl. Especially preferred for Ar$^1$—CH—Ar$^2$ is diphenylmethyl.

The preferred groups for X are C$_1$–C$_6$ alkyl having one or two substituents selected from hydroxy, halogen, C$_1$–C$_6$ alkoxy, C$_2$–C$_6$ alkanoyl, C$_2$–C$_6$ alkanoyloxy, C$_1$–C$_6$ alkylthio, mono C$_1$–C$_6$ alkylamino, di C$_1$–C$_6$ alkylamino, amino, cyano and azido. More preferred for X is C$_1$–C$_6$ alkyl having one or two substituents selected from hydroxy, C$_1$–C$_6$ alkoxy and C$_1$–C$_6$ alkylthio. Especially preferred groups for X are —C(CH$_3$)$_2$OH, —C(OH)(CH$_3$)CH$_2$OH, —C(CH$_3$)$_2$OCH$_3$ or —C(CH$_3$)$_2$SCH$_2$CH$_3$.

The preferred group for Y is hydrogen or Z—(CH$_2$)$_p$—. Especially preferred group for Y is hydrogen or carboxy.

A particularly preferred sub-group of compounds of the invention consists of the compounds of formula I, wherein Ar$^1$ and Ar$^2$ are each phenyl; R is methyl and the OR group is at the 2 position; X is —C(CH$_3$)$_2$OH, —C(OH)(CH$_3$)CH$_2$OH, —C(CH$_3$)$_2$OCH$_3$ or —C(CH$_3$)$_2$SCH$_2$CH$_3$; and Y is hydrogen or carboxy at the 5- or 6 position.

The preferred stereochemistry of the compound of the invention is:

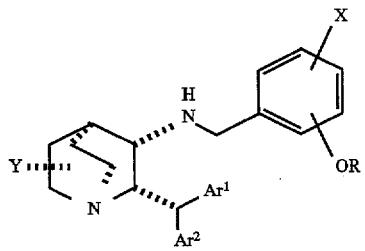

Preferred individual compounds of the present invention are:

(2S,3S )-N-[5-(1-hydroxy-1-methylethyl-)-2-methoxyphenyl]methyl-2-diphenylmethyl-1-azabicyclo[2.2.2]octan-3-amine;

(2S,3S)-N-[2-methoxy-5-(1-methoxy-1-methylethyl)phenyl]methyl-2-diphenylmethyl-1-azabicyclo[2.2.2]octan-3-amine;

(3R,4S,5S,6S)-3-[5-(1-hydroxy-1-methylethyl)-2-methoxyphenyl]methylamino-6-diphenylmethyl-1-azabicyclo[2.2.2]octan-5-carboxylic acid;

(2S,3S)-2-diphenylmethyl-N-[5-(1-hydroxy-1-hydroxymethylethyl)-2-methoxyphenyl]methyl-1-azabicyclo[2.2.2]octan-3-amine;

(3R,4S,5S,6S)-3-[5-(1-methoxy-1-methylethyl)-2-methoxyphenyl]methylamino-6-diphenylmethyl-1-azabicyclo [2.2.2]octan-5-carboxylic acid;

(3R,4S,5S,6S)-3-[5-(1-hydroxy-1-methylethyl)-2-methoxyphenyl]methylamino-6-diphenylmethyl-1-azabicyclo[2.2.2]octan-5-carboxylic acid; and (3R,4S,5S,6S)-3-[5-(1-ethylthio-1-methylethyl)-2-methoxyphenyl]methylamino-6-diphenylmethyl-1-azabicyclo[2.2.2]octan-5-carboxylic acid.

The compounds of formula I may form acid addition salts. The pharmaceutically acceptable acid addition salts are those formed from acids which form non-toxic acid salts.

The novel heteroatom substituted alkyl benzylaminoquinuclidines of formula I of this invention may be prepared by a number of synthetic methods well known by those skilled in the art.

Thus, the following routes 1 and 2 (indicated in the following equations) are available to prepare the objective compounds of the present invention:

Equation 1

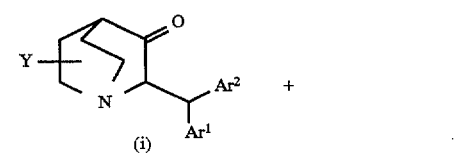

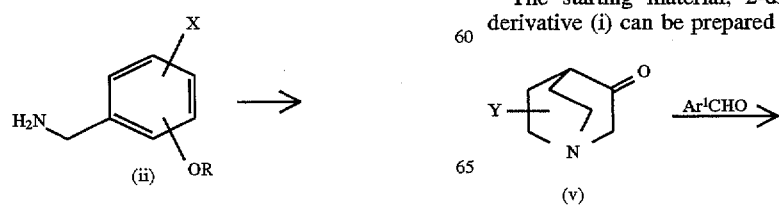

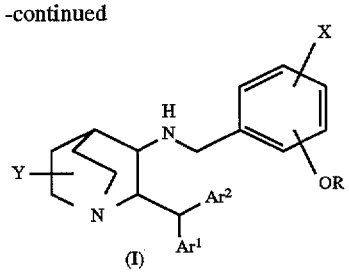

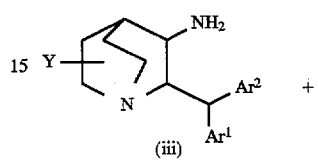

Equation 2

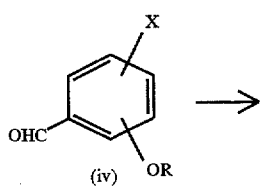

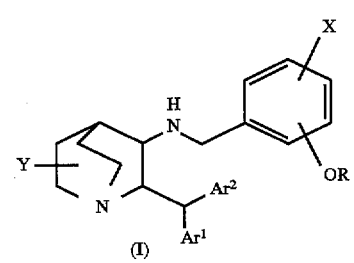

The first route in Equation 1 is through the condensation of a 2-diarylmethylquinuclidine-3-one (i) and a substituted benzylamine (ii), and subsequent reduction of a resulting intermediate, an imine.

This transformation is accomplished by, first, formation of an imine with (i) and a corresponding benzylamine (ii), in most cases, catalyzed by acid (e.g. camphor sulfonic acid) in hot toluene under a dehydrating conditions. Then, the imine is reduced to afford compound (I). This reduction can be carried out by catalytic hydrogenation, or with several hydride reagents such as aluminum-based reagents, boranes, borohydrides or trialkylsilanes. In most of the cases, the reaction with trialkylboranes (e.g. 9-BBN) NaBH$_4$, NaBH$_3$CN or NaBH(OAc)$_3$ in a reaction inert solvent such as methylene chloride, THF, methanol, acetonitrile, DMF etc. in the presence of acid catalyst such as acetic acid at room temperature for several minutes to a few days gives satisfactory results. The above two reaction steps can be also carried out without isolation of the imine intermediate. Reductive amination employing NaBH$_3$CN in methanol in the presence of acetic acid is a effective procedure.

The starting material, 2-diarylmethylquinuclidin-3-one derivative (i) can be prepared according to the equation 3:

Equation 3

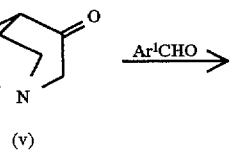

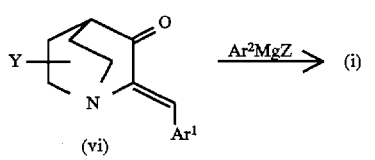

The quinuclidin-3-one (v) can be prepared from properly substituted isonicotinates by the same method as unsubsti-

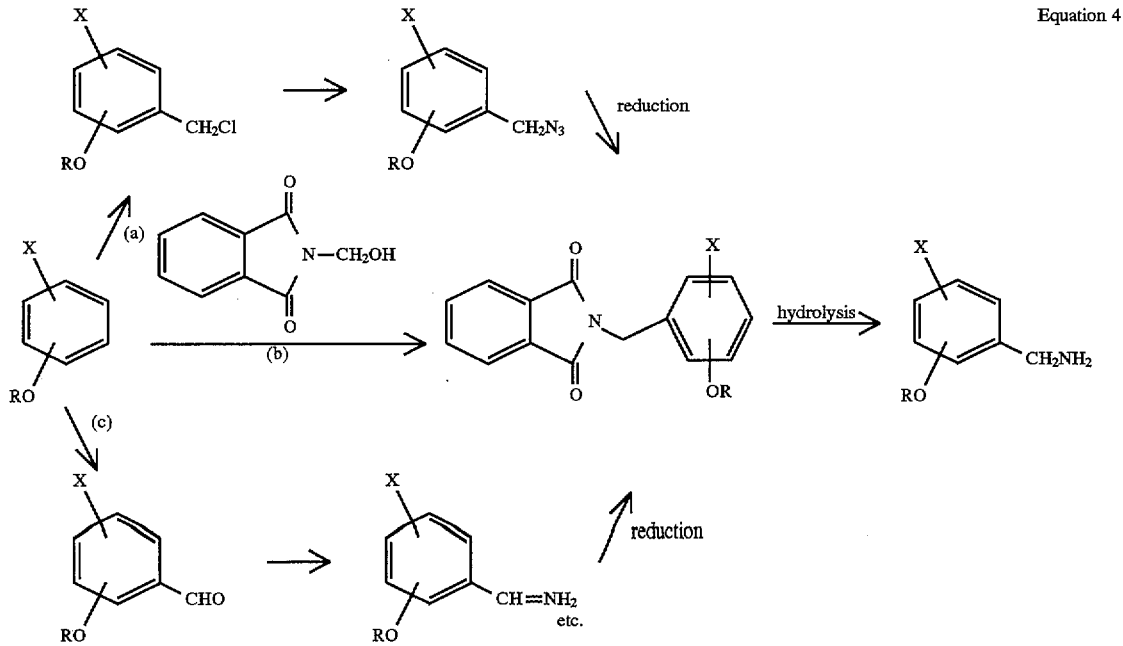

Equation 4 tuted quinuclidine-3-one reported in Org. Synth. Coll. Vol., V, 989 (1973). For example, 5-methyl-, 5-methoxycarbonyl-, 5-carbamoyl, 5-dimethylaminocarbonyl-, 6-dimethylaminocarbonyl-, 5-diethylaminocarbonyl-, 6-diethylaminocarbonyl-, 5-carboxy-, 4-allyl- and 6-phenethylquinuclidin-3-ones have already been prepared by this method (*J. Chem. Soc. Perkin Trans.*, 1, 409 (1991) and WO 92/20676).

Introduction of $Ar^1Ar^2CH$— group such as benzhydryl or its congener at the 2-position of a quinuclidine-3-one (v) can be performed by following the procedure reported in *J. Med. Chem.*, 18, 587 (1975).

Compound (v) can be converted to the 2-aryliden compound (vi) by aldol condensation with an aromatic aldehyde ($Ar^1CHO$) catalyzed by a base such as sodium hydroxide in a protic solvent (e.g. ethanol) heating at its reflux temperature. Introduction of another aryl group ($Ar^2$) can be carried out by the Grignard reaction in an aprotic solvent such as THF, ether or toluene. In order to improve the yield for the 1, 4-addition product, an addition of catalytical amount of copper(I) halide such as cuprous bromide or cuprous iodide gives satisfactory results. The reactions are usually conducted at low temperature such as from −78° to 0° C. Alternatively, the procedure reported by Kuwajima (*Tetrahedron*, 45, 349 (1989)) employing trimethylsilylchloride, HMPA and CuBr-DMS is also preferred in some cases to improve the selectivity.

The substituted benzylamine (ii) in Equation 1 can be prepared according to methods well known by those skilled in the art such as (a) chloromethylation/azido-replacement/reduction, (b) amidomethylation/hydrolysis and (c) formylation/imine, hydrazone, oxime, etc./reduction (See equation 4 and WO 92/20676).

The second route to obtain the compounds of the present invention (I) in Equation 2 is through the condensation of 3-amino-2-diarylmethylquinuclidine (iii) and a substituted benzaldehyde (iv) followed by reduction.

The starting material, 3-aminoquinuclidine derivative (iii) in equation 2 can be synthesized in a similar manner with Journal of Medicinal Chemistry, Vol. 18, p. 587 (1975). The reaction is shown in Equation 5.

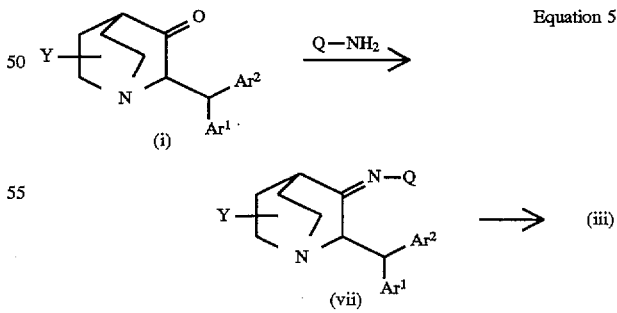

Equation 5 wherein Q is $NH_2$, $NMe_2$, OH or $CH_2C_6H_5$.

The compound (vii) is an imino-type derivative such as oxime, hydrazone or imine, and it can be formed by reaction of (i) with the corresponding ammonia or primary amines (Q—$NH_2$) (e.g. hydroxylamines (Q=OH), N,N-dimethylhydrazone (Q=$NMe_2$), or benzylamine (Q=$CH_2$Ph)). The obtained product (vii) is reduced with a variety of reducing reagents such as lithium alminium hydride, borane reagent, catalytic hydrogenation or combination of such conditions. In the case of imines derived from ammonia, formic acid can be used as a reductant.

The formed 3-amino derivative (iii) is, then, arylmethylated with a proper benzaldehyde (iv) under an ordinary condition for reductive amination (e.g. sodium cyanoborohydride in methanol; *J. Am. Chem. Soc.*, 93, 2897 (1971)). Several other reducing agents such as $NaBH_4$, $NaBH(OAc)_3$ or trialkylsilanes can be also used to perform this transformation.

In case of preparing the substituted benzaldehyde (iv), the standard methods well known to those skilled in the art from the following literature can be used: (A) Duff's reaction (hexamethylenetetramine/TFA), *Synth. Commun.*, 15, 61 (1985), (B) TiCl/dichloromethylether, *J. Org. Chem.*, 51, 4073 (1986), (C) A process by two step reaction (HCl, HCHO, then 2-nitropropane, NaOMe), JP-58-501127 and (D) Vilsmeier reaction.

Equation 6

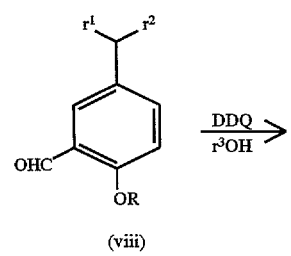

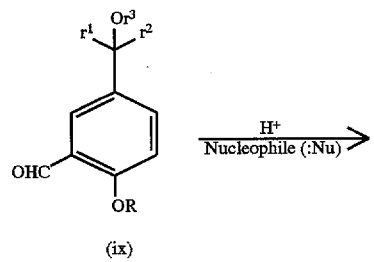

wherein R, $r^1$ and $r^2$ are each independently alkyl, $r^3$ is alkyl or hydrogen, and Nu is the corresponding nucleophile with substituent having heteroatom.

The substituted benzaldehyde obtained here can be convened to other benzaldehydes by well-known methods to those skilled in the art. For example, the benzyl position of the compound which has an electrodonating group on the benzene ring is easy to oxidize and various kinds of substituent can be introduced by oxidant DDQ under adequate nucleophile (A. B. Turner et al., J. Chem. Soc. Chem. Commun., 126 (1975); T. Mukaiyama et al., Chem. Lett., 1811 (1987); A. Guy et al., Synthesis, 900 (1988); O. Yonemitsu et al., Chem. Pharm. Bull., 36, 4244 (1988)). Thus as shown in Equation 6, benzaldehyde (viii) is oxidized by DDQ at room temperature in the presence of water to give the hydroxy compound (ix). The compound (ix) is subjected to nucleophile in the presence of acid catalyst to give the aldehyde (x) which has various kinds of substituents at the benzyl position. The oxidation reaction using DDQ is carried out in the presence of an adequate nucleophile such as an alcohol, alkylthiol, TMS-azide, TMSCN, enolesilylether, ketenesilylacetal, alkylsilane or aryltin to give directly the aldehyde which has a various kind of substituent at the benzyl position (See Equation 7).

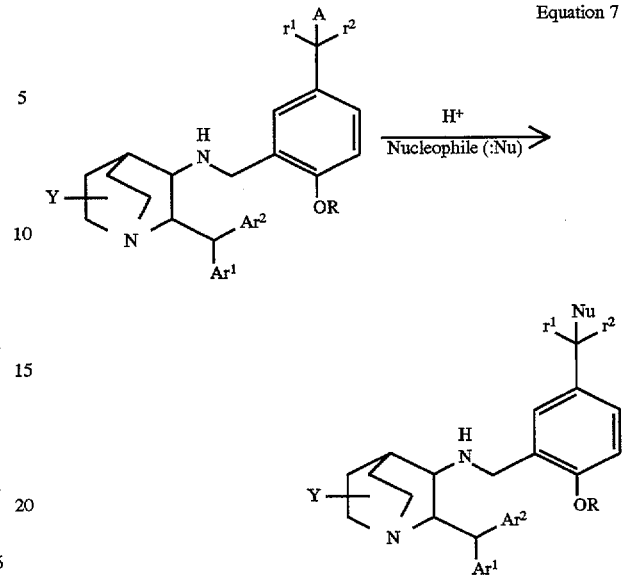

Equation 7 wherein A is the group which can be subjected to nucleophilic substitution reaction such as hydroxy or alkoxy and the other symbol are the same as defined in Equation 6.

Oxidation of a double bond is also useful for the synthesis of other X groups. The oxidation agent such as $OsO_4$/N-methylmorphorine N-oxide can be used. Such example is described in Equation 8.

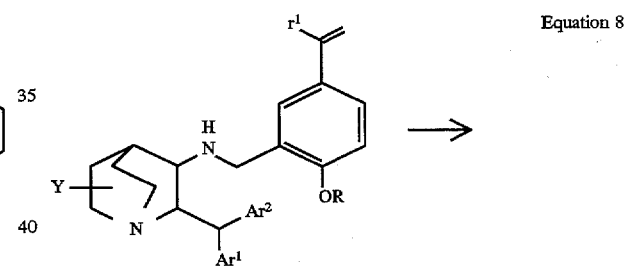

Equation 8

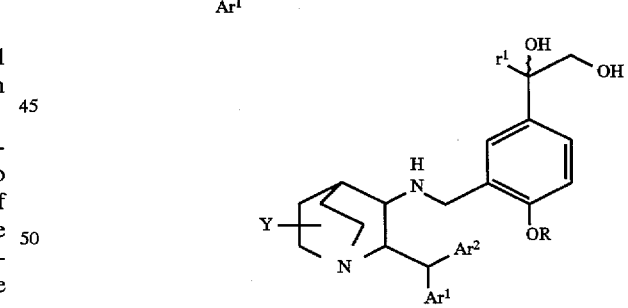

The side chain (Y) on the quinuclidine ting in the objective compound (I) can be converted into other Y groups by chemical modification which is well known to those skilled in the art.

For example, a compound having a group Y in which an amide is contained can be converted to the corresponding amine derivative with a reducing reagent such as lithium alminium hydride, and also to the corresponding carboxylic acid by hydrolysis.

The obtained carboxylic acid can be also converted to the corresponding ester by a standard procedure such as an acid or base catalyzed esterification in adequate alcohol or methylation by diazomethane. A compound having an ester or carboxylic acid included in Y can be converted to the corresponding hydroxymethyl by treating with a suitable reducing agent such as lithium alminium hydride. A reaction-inert solvent such as dichloromethane, ether, THF, alcohols, dimethylformamide and toluene are suitable in the above reaction.

In addition, a compound having protected amino acid (W—$(CH_2)_m$—$CHR^2$—$(CH_2)_n$—$NR^1CO$—) in Y can be synthesized by a various conventional methods for peptide synthesis as described in "Peptide synthesis, the basis and experiments" edited by N. Izumiya, 1985 (Maruzen).

For instance, those methods include an activated ester method with acid chloride or mixed acid anhydride, and a condensation method employing an appropriate condensing agent which is selected from dicyclohexylcarbodiimide (DCC), water soluble carbodiimide, 2-ethoxy-N-ethoxycarbonyl-1,2dihydroquinoline, Bop agent, diethyl azodicarboxylate-triphenylphosphine, diethylcyanophosphonic acid and diphenylphospholylazide and the like. A reaction-inert solvent such as dichloromethane, THF, dimethylformamide and toluene are suitable in the condensation reaction. If necessary, addition of tertiary amine such as triethylamine can promote the condensation reaction. Furthermore, in order to prevent racemization, employment of N-hydroxysuccinimide, N-hydroxybenzotriazoleor3,4-dihydro-3-hydroxy-4-oxo-1,2,3-benzotriazine etc. can bring a preferable result in this reaction.

If the benzylamine part interferes such transformation, appropriate protection of NH group is necessarry. For such protection, Cbz or Boc group is suitable (c.f. T. W. Greene, "Protective Groups in Organic Synthesis", J. Wiley & Sons (1981)). After finishing transformation of the functional group, the protecting group is removed by a suitable standard procedure to provide the objective compound. The above side chain conversion-reaction, in advance, can be also adopted in the intermediate compounds such as ketones (i), (v) or (vi) or amine (iii).

The products with various side chain (Y) on the quinuclidine ring, such as methoxycarbonyl, carbamoyl, ethylaminocarbonyl, N-methoxy-N-methylaminocarbonyl, dimethylaminocarbonyl, diethylaminocarbonyl, morpholinocarbonyl, thiamorpholinocarbonyl, (4-sulfoxypiperidino)carbonyl, (4-sulfodioxypiperidino) carbonyl, carboxy, hydroxymethyl, allyl and phenethyl, carbamoylmethyl, carboxymethyl, N-(2-carbamoylpyrrolidin-1-yl)carbonyl, N-(1-carbamoylethyl) carbamoyl, N-(carbamoylmethyl)carbamoyl, N-(1-carbamoyl-3-methylbutyl)carbamoyl, N-(2-carbamoylethyl) carbamoyl, N-(1-carbamoyl-2-phenethyl)carbamoyl, N,N-bis(cyanomethyl)carbamoyl, have already been reported WO 90/05729, WO 92/20676 and JP application No. 307179/92).

The reaction temperatures for the reactions in Equations 1 and 2 are preferably in the range of ice-cooled temperature to the reflux temperature of the solvent, e.g., 5°–100° C., but if necessary, temperatures lower or higher can be adopted. The reactions are easily monitored by TLC. The reaction time is in general from a few minutes to several hours.

The compounds of formula I can be isolated and purified by conventional procedures, such as recrystallisation or chromatographic purification.

As the quinuclidine compounds of this invention all possess at least two asymmetric center, they are capable of occurring in various stereoisomeric forms or configurations. Hence, the compounds can exist in separated (+)- and (−)-optically active forms, as well as in racemic or (±)-mixtures thereof. The present invention includes all such forms within its scope. For instance, the diastereomers can be obtained by methods well known to those skilled in the art, e.g., by separation of mixtures by fractional crystallization or chromatographic separation, asymmetric synthesis and the like. Hence, when those skilled in the art use the compounds of this invention, they may choose any desired isomers, such as optical isomers and diastereomers, or mixtures thereof, from among the objective compounds of the present invention.

In so far as the quinuclidine compounds of this invention are basic compounds, they are all capable of forming a wide variety of different salts with various inorganic and organic acids. Although such salts must be pharmaceutically acceptable for administration to animals, it is often desirable in practice to initially isolate the quinuclidine base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acid which are used to prepare the pharmaceutically acceptable acid addition salts of the aforementioned quinuclidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, ptoluenesulfonate and pamoate (i.e., 1.1'-methylene-bis-(2-hydroxy-3-naphthoate))salts.

The quinuclidine compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques.

The chemical bases which are used as reagents to prepare the pharmaceutically acceptable base salts of this invention are those which form non-toxic base salts with the herein described acidic quinuclidine derivatives. These particular non-toxic base salts include those derived form such pharmaceutically acceptable cations as sodium, potassium, calcium and magnesium, etc. These salts can easily be prepared by treating the aforementioned acidic quinuclidine compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active quinuclidine compounds of the present invention exhibit substance P receptor-binding activity and therefore, are of value in the treatment of a wide variety of clinical conditions which are characterized by the presence of an excess of said substance P activity. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, respiratory diseases such as asthma, as well as pain in any of the aforesaid conditions, including migraine. Hence, these compounds are readily adapted to therapeutic use as substance P antagonists for the control and/or treatment of any of the aforesaid clinical conditions in mammals, including humans.

The compounds of the present invention are particularly useful as antiinflammatory agents. They exhibit a significant degree of activity in the mustard oil-induced rat foot edema test [described by A. Nagahisa et al., *European Journal of Pharmacology*, 217, 191 (1992)].

The radiolabelled quinuclidine compounds of the formula are useful as research and diagnostic tools in metabolism pharmacokinetic studies and in binding assays with the drug in both animal and human. Specific applications in research include radioligand binding assays, autoradiography studies and in vivo binding studies, while specific applications in the diagnostic area include studies of substance P receptor in the human brain, such as up/down regulation in a diseases state, and in vivo binding in the relevant tissues for inflammation, e.g., immune-type cell or cells that are directly involved in inflammatory bowel disorders and the like. Specifically, the radiolabelled forms of the quinuclidine compounds are the tritium and $^{14}C$-isotopes of substituted 3-aminoquinuclidine in this invention.

The quinuclidine compounds of the formula I of this invention can be administered via either the oral, parenteral or topical routes to mammals. In general, these compounds are administered to humans in doses ranging from about 3 mg up to 750 mg per day. Variations will occur depending upon the disease state being treated, the species of animal being treated and its individual response to said medicament, as well as on the type of pharmaceutical formulation chosen and the time period and interval at which such administration is carried out. However, a dosage level that is in the range of from about 0.06 mg to about 2 mg per kg of body weight per day is most desirably employed for oral treatment of an inflammatory disease in a human subject.

The compounds of the present invention may be administered alone or in combination with pharmaceutically acceptable carriers or diluents by either of the above routes previously indicated, and such administration can be carried out in single or multiple doses. More particularly, the novel therapeutic agents of of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in CHO-cells which reveal NK1 receptor or IM-9 cells employing radioactive ligands. The substance P antagonist activity of the herein described quinuclidine compounds is evaluated by using the standard assay procedure described by M. A. Cascieri et al., as reported in the *Journal of Biological Chemistry*, 258, 5158 (1983). This method essentially involves determining the concentration of the individual compound required to reduce by 50% the amount of radiolabelled substance P ligands at their receptor sites in said isolated cow tissues or IM-9 cells, thereby affording characteristic $IC_{50}$ values for each compound tested. In this test, some preferred compounds indicated low $IC_{50}$ values of less than 0.1 nM with respect to inhibition of binding at its receptor.

Alternatively, the antiinflammatory activity of the compounds of the present invention is demonstrated by a capsaicin-indused plasma extravasation test. In this test, antiinflammatory activity is determined as the percent inhibition of plasma protein extravasation in the ureter of male Hartley quinea pigs (weighing 300–350 g) in response to the intraperitoneal injection of capsaicin into anesthetized animals. The compounds of the present invention are dissolved in 0.1% methyl cellulose/water and dosed orally 1 h before capsaicin challenge. Evans Blue dye (30 mg/kg) is administered intravenously 5 min before capsaicin challenge. The animals are killed 10 min after capsaicin injection and both right and left ureters are removed. The Evans Blue dye is extracted and determined colorimetrically.

In the above two tests, compounds are considered active if the difference in response between the drug-treated animals and a control group receiving the vehicle alone is statistically significant. In those test, some preferred compounds indicated high percentage with respect to inhibition of plasma protein extravasation.

The anti-psychotic activity of the compounds of the present invention as neuroleptic agents for the control of various psychotic disorders can be determined by a study of their ability to suppress substance P-induced hypermotility in rats. This study is carried out by first dosing the rats with a control compound or with an appropriate test compound of the present invention, then injecting the rats with substance P by intracerebral administration via canula and thereafter measuring their individual locomotor response to said stimuli.

EXAMPLES

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in CDCl$_3$ by a JEOL NMR spectrometer (JNM-GX270, 270 MHz for $^1$H, 67.5 MHz for $^{13}$C) unless otherwise indicated and peak positions are expressed in parts per million (ppm) downfield from tetramethylsilane. The peak shapes are denoted as follows: s, singlet; d, doublet; t, triplet; m, multiplet; br, broad.

Example 1

Preparation of (2S,3S)-N-[5-(1-hydroxy-1-methylethyl)-2-methoxyphenyl]methyl-2-diphenylmethyl-1-azabicyclo[2.2.2]octan-3-amine (i) 5-(1-Hydroxy-1-methylethyl)-2-methoxybenzaldehyde and 5-(1-methoxy-1-methylethyl)-2-methoxybenzaldehyde DDQ (10.07 g, 44.36 mmol) was added to a solution of 5-isopropyl-2-methoxybenzaldehyde (2.63 g, 15.3 mmol) dissolved in methylene chloride (100 ml) contained water (10 ml) at room temperature, and the resulting mixture was stirred for 24 h. Ether (200 ml) was added to the reaction mixture, and insoluble materials were removed by filtration. The filtrate was washed with aq. sodium thiosulfate solution, aq. sodium carbonate solution, and brine, successively and dried over magnesium sulfate. After evaporation of the solvent the resultant yellow oil was purified by chromatography (silica gel, 2–70% ethyl acetate/hexane) to afford pure 5-(1-hydroxy-1-methylethyl)-2-methoxybenzaldehyde (498 mg, 17%) as a slightly yellow oil and 5-(1-methoxy-1-methylethyl)-2-methoxybenzaldehyde (less polar, 129 mg, 4%) as a solid.

5-(1-hydroxy-1-methylethyl)-2-methoxybenzaldehyde:

$^1$H NMR δ 10.47 (s, 1H), 7.90 (d, J=2.6 Hz, 1H), 7.77 (dd, J=8.8, 2.6 Hz, 1H), 6.98 (d, J=8.8 Hz, 1H), 3.94 (s, 3H), 1.58 (s, 6H).

5-(1-methoxy-1-methylethyl)-2-methoxybenzaldehyde:

$^1$H NMR δ 10.48 (s, 1H), 7.83 (d, J=2.6 Hz, 1H), 7.67 (dd, J=8.8, 2.6 Hz, 1H), 7.00 (d, J=8.8 Hz, 1H), 3.94 (s, 3H), 3.04 (s, 3H), 1.52 (s, 6H).

(ii)(2S,3S)-N-[5-(1-hydroxy-1-methylethyl)-2-methoxyphenyl]methyl-2-diphenylmethyl-1-azabicyclo[2.2.2]octan-3-amine Sodium triacetoxyborohydride (858 mg, 3.99 mmol) was added to a solution of (2S,3S)-2-diphenylmethyl-1-azabicyclo[2.2.2]octane-3-amine(743 mg, 2.54 mmol) and 5-(1-hydroxy-1-methylethyl)-2-methoxybenzaldehyde (488 mg, 2.52 mmol) dissolved in methylene chloride (10 ml) at room temerature, and the resulting solution was stirred for 4.5 h. The reaction mixture was diluted with methylene chloride, and washed with aq. sodium bicarbonate solution and brine. The extracts were dried over magnesium sulfate, and concentrated by evaporation. The residual oil was purified by crystallization from methylene chloride to yield analytically pure sample of the title compound as a solvated compound with methylene chloride (660 mg, 47%).

mp 89.4°–93.2° C.;

IR (CH$_2$Cl$_2$) 3600, 1500 cm$^{-1}$;

$^1$H NMR δ 7.35–7.03 (m, 11H), 6.97 (d, J=2.6 Hz, 1H), 6.67 (d, J=8.4 Hz, 1H), 5.30 (A peak derive from methylene chloride) 4.50 (d, J=12.1 Hz, 1H), 3.68 (m, 1H), 3.61 (d, J=12.8 Hz, 1H), 3.54(s, 3H), 3.25–3.15 (m, 1H), 3.18 (d, J=12.8 Hz, 1H), 2.93 (dd, J=7.7, 4.4 Hz, 1H), 2.78 (m, 2H), 2.60 (m, 1H), 2.10 (br. s, 1H), 1.93 (m, 1H), 1.70–1.45 (m, 2H), 1.55 (s, 3H), 1.54 (s, 3H), 1.27 (m, 1H);

$^{13}$C NMR 156.2, 145.7, 143.4, 140.6, 128.8, 128.2, 127.7, 127.52, 127.50, 126.2, 125.9, 125.7, 123.7, 109.5, 72.0, 61.7, 55.3, 55.0, 53.4 (A peak derive from methylene chloride), 49.4, 49.1, 47.3, 41.9, 31.8, 31.7, 25.6, 24.9, 19.9.

Example 2

Preparation of (2S,3S)-N-[5-(1-hydroxy-1-methylethyl)-2-methoxyphenyl]methyl-2-diphenylmethyl-1-azabicyclo[2.2.2]octan-3-amine monobenzenesulfonate To a stirred solution of (2S,3S)-N-[5-(1-hydroxy-1-methylethyl)-2-methoxyphenyl]methyl-2-diphenylmethyl-1-azabicyclo[2.2.2]octan-3-amine (170 mg, 0.306 mmol) in anhydrous methanol (5 ml) was added benzenesulfonic acid (48.4 mg, 0.306 mmol) in anhydrous methanol (5 ml) dropwise at 0° C. The solvent was evaporated in vacuo, and the residue was crystallized from i-propanol to afford CJ-12, 764-26 (141 mg, 64.6%) as a white crystal.

mp: 253°–255° C.;

IR(KBr): 3,430, 2,980, 1,505, 1,499, 1,249, 1,200, 1,176, 1,126, 1,032, 1,017, 753, 717, 614, 562 cm$^{-1}$.

Example 3

Preparation of (2S,3S)-N-[2-methoxy-5-(1-methoxy-1-methylethyl)phenylmethyl]-2-diphenylmethyl-1-azabicyclo[2.2.2]octan-3-amine Sodium triacetoxyborohydride (152 mg, 0.707 mmol) was added to a solution of (2S,3S)-2-diphenylmethyl-1-azabicyclo[2.2.2]octane-3-amine(135 mg, 0.462 mmol) and 5-(1-methoxy-1-methylethyl)-2-methoxybenzaldehyde prepared in example 1 (92 mg, 0.442 mmol) dissolved in methylene chloride (4 ml) at room temerature, and the resulting solution was stirred for 4 h. The reaction mixture was diluted with methylene chloride, and washed with aq. sodium bicarbonate solution and brine. The extracts were dried over magnesium sulfate, and concentrated by evaporation. The residual oil was purified by crystallization from methylene chloride to yield analytically pure sample of the title compound as a white crystal (94 mg, 42%).

mp: 126.8°–127.1° C.;

IR (CH$_2$Cl$_2$) 1500, 1070 cm$^{-1}$;

$^1$H NMR δ 7.33–7.03 (m, 11H), 6.96 (d, J=2.2 Hz, 1H), 6.65 (d, J=8.6 Hz, 1H), 4.50 (d, J=12.2 Hz, 1H), 3.69–3.61 (m, 2H), 3.52 (s, 3H), 3.25–3.14 (m, 2H), 3.03 (s, 3H), 2.89 (dd, J=7.6, 3.9 Hz, 1H), 2.76 (m, 2H), 2.59 (m, 1H), 2.09 (m, 1H), 1.92 (m, 1H), 1.72–1.40 (m, 2H), 1.50 (s, 3H), 1.49 (s, 3H), 1.30–1.20 (m, 1H).

Example 4

Preparation of (2S,3S)-N-[2-methoxy-5-(1-ethylthio-1-methylethyl)phenyl]methyl-2-diphenylmethyl-1-azabicyclo[2.2.2]octan-3-amine DL-10 camphorsulfonic acid (47 mg, 0.202 mmol) was added to a solution of ethanethiol (0.10 ml, 1.35 mmol) and (2S,3S)-N-[5-(1-hydroxyethyl-1-methyl)-2-methoxyphenyl]methyl-2-diphenylmethyl-1-azabicyclo[2.2.2]octan-3-amine (a solvate with 1.0 methylene chloride) (50.5 mg, 0.0909 mmol) dissolved in anhydrous acetonitrile (5 ml) at rt. After 24 h the reaction mixture was quenched with triethylamine (1 ml), and concentrated by evaporation. The residue was diluted with methylene chloride and aq. sodium bicarbonate, and the organic layer was dried over magnesium sulfate. After evaporation of the solvent residual oil was purified with chromatography (ICN alumina N, super I, 25–100% ethyl acetate/hexane) followed by recrystalization from isopropanol to afford the title compound (15 mg, 32%).

IR ($CH_2Cl_2$)1500 $cm^{-1}$;

$^1$H NMR δ 7.33–7.04 (m, 12H), 6.61 (d, J=8.6 Hz, 1H), 4.51 (d, J=12.2 Hz, 1H), 3.65 (m, 1H), 3.61 (d, J=12.9 Hz, 1H), 3.50 (s, 3H), 3.18 (m, 1H), 3.16 (d, J=12.9 Hz, 1H), 2.89 (dd, J=7.6, 4.4 H, 1H), 2.75 (m, 2H), 2.59 (m, 1H), 2.24 (quartet, J=7.5 Hz, 2H), 2.08 (m, 1H), 1.92 (m, 1H), 1.66 (s, 6H), 1.70–1.47 (m, 2H), 1.27 (m, 1H), 1.10 (t, J=7.5 Hz, 3H).

Example 5

Preparation of (2S,3S)-2-diphenylmethyl-N-[5-(1-hydroxy-1-(hydroxymethyl)ethyl)-2-methoxyphenyl]methyl-1-azabicyclo[2.2.2]octan-3-amine (2S,3S)-2-Diphenylmethyl-N-[5-(propen-2-yl)-2-methoxyphenyl]methyl-1-azabicyclo[2.2.2]octan-3-amine (267 mg, 0.590 mml) and N-methylmorphorine N-oxide (145 mg, 1.24 mmol) were disolved in acetonitrile (6 ml) and water (3 ml). To this was added a solution of osumium tetroxide (0.1M, in t-butanol, 0.59 ml, 0.059 mmol) at room temperature. After the reaction mixture was stirred for 3 h, the most of the solvent (acetonitrile) was removed by evaporation. The aqueous residue was basified to pH 10.5 with aq. sodium carbonate aolution, and extracted with methylene chloride. The organic extracts were dried over magunesium sulfate. After concentration the crude products were purified by chromatography (Aluminum oxide 90, Merck 70–230 mesh, 25%–100% ethylacetate/hexane, then 0–10% methanol/ethylacetate) to afford 166 mg of the title compound as amorphous solid.

mp 65.5°–82.8° C.;

$^1$H NMR δ 7.35–7.05 (m, 11H), 6.93 (d, J=1.5 Hz, 1H), 6.70 (d, J=8.8 Hz, 1H), 4.50 and 4.49 (two d, J=12 Hz, total 1H), 3.74–3.53 (m, 5H), 3.54 and 3.53 (two s, total 3H), 3.25–3.13 (m, 2H), 2.95 (dd, J=8, 4 Hz, 1H), 2.75 (m, 2H), 2.58 (m, 1H), 2.09 (m, 1H), 1.95–1.20 (m, 4H), 1.49 (s, 3H).

Example 6

Preparation of (3R,4S,5S,6S)-3-[5-(1-hydroxy-1-methylethyl)-2-methoxyphenyl]methylamino-6-diphenylmethyl-1-azabicyclo[2.2.2]octan-5-carboxylic acid (1) (3R,4S,5S,6S)-5-amino-6-diphenylmethyl-1-azabicyclo[2.2.2]octane-3-carboxylic acid dihydrochloride A mixture of (3R,4S,5S,6S)-5-(5-isopropyl-2-methoxybenzylamino)-6-diphenylmethyl-1-azabicyclo[2.2.2]octane-3-carboxylic acid dihydrochloride (500 mg, 0.88 mmol) and Pd-C (10%, 500 mg) in water (20 mL) was stirred under $H_2$ atmosphere (50 atm) at rt for 20 h. The catalyst was filtered off by filtration, and the filtrate was concentrated to give the title compound as a pale yellow solid (200 mg, 0.49 mmol, 54%).

mp: 270° C. (dec);

$^1$H NMR (DMSO-$d_6$) δ 8.57 (br, 2H), 8.24 (br, 1H), 7.75–7.22 (m, 10H), 5.70–5.38 (m, 2H), 4.30–2.80 (m, 9H), 2.20–1.70 (m, 2H).

(ii) (3R,4S,5S,6S)-3-[5-(1-hydroxy-1-methylethyl)-2-methoxyphenyl]methylamino-6-diphenylmethyl-1-azabicyclo[2.2.2]octan-5-carboxylic acid A mixture of (3R,4S,5S,6S)-5-amino-6-diphenylmethyl-1-azabicyclo[2.2.2]octane-3-carboxylic acid dihydrochloride (100 mg, 0.25 mmol), 5-(1-hydroxy-1-methylethyl)-2-methoxybenzaldehyde (60 mg, 0.3 mmol), and NaBH$_3$CN (25 mg, 0.4 mmol) was stirred at rt for 17 h. The solvent was removed. The resulting solid was dissolved in water (5mL), and passed through the column filled by hydrophorbic interaction chromatography to give a solid (80 mg). This solid was purified by column chromatography on RP-silicagel (cosmosil 40C18-PREP, 15 g) to give the title compound (30 mg, 0.05 mmol, 20%)

mp: 150.0°–153.0° C.;

$^1$H NMR δ 7.45–6.65 (m, 13H), 4.55 (d, J=12 Hz, 1H), 4.20–2.53 (m, 11H), 3.48 (s, 3H), 2.10–1.30 (m, 3H), 1.54 (s, 6H).

I claim:

1. A compound of the chemical formula (I) and its pharmaceutically acceptable salt:

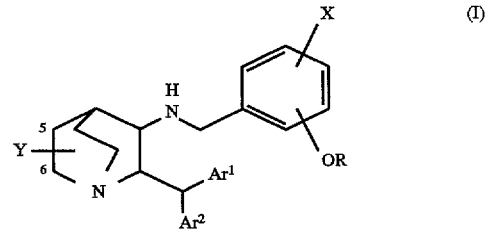

wherein

R is methyl and the OR group is at the 2-position;

X is ($C_2$–$C_6$)alkyl having one or two substituents selected from hydroxy, ($C_1$–$C_6$)alkoxy and ($C_1$–$C_6$)alkylthio;

$Ar^1$ and $Ar^2$ are each phenyl, monochlorophenyl or monofluorophenyl; and

Y is hydrogen or carboxy; and Y is at the 5- or 6-position.

2. A compound according to claim 1, wherein X is —C(CH$_3$)$_2$OH, —C(OH)(CH$_3$)CH$_2$OH, —C(CH$_3$)$_2$OCH$_3$ or —C(CH$_3$)$_2$SEt; and $Ar^1$ and $Ar^2$ are each phenyl.

3. A compound according to claim 2 selected from (2S,3S)-N-[5-(1-hydroxy-1-methylethyl)-2-methoxyphenyl]methyl-2-diphenylmethyl-1-azabicyclo[2.2.2]octan-3-amine;

(2S,3S)-N-[2-methoxy-5-(1-methoxy-1-methylethyl)phenyl]methyl-2-diphenylmethyl-1-azabicyclo[2.2.2]octan-3-amine;

(2S,3S,4S,5R)-3-[5-(1-hydroxy-1-methylethyl)-2-methoxyphenyl]methylamino-2-diphenylmethyl-1-azabicyclo[2.2.2]octan-5-carboxylic acid;

(2S,3S)-2-diphenylmethyl-N-[5-(1-hydroxy-1-hydroxymethylethyl)-2-methoxyphenyl]methyl-1-azabicyclo[2.2.2]octan-3-amine;

(2S,3S,4S,5R)-3-[5-(1-methoxy-1-methylethyl)-2-methoxyphenyl]methylamino-2-diphenylmethyl-1-azabicyclo[2.2.2]octan-5-carboxylic acid;

(2S,3S,4S,5R)-3-[5-(1-hydroxy-1-methylethyl)-2-methoxyphenyl]methylamino-2-diphenylmethyl-1-azabicyclo[2.2.2]octan-5-carboxylic acid; and (2S,3S,4S,5R)-3-[5-(1-ethylthio -1-methylethyl)-2-methoxyphenyl]methylamino-2-diphenylmethyl-1-azabicyclo[2.2.2]octan-5-carboxylic acid.

4. A method for antagonizing substance P in a mammalian subject, which comprises administering to the said subject an effective amount of a compound of claim 1.

5. A method for treating or preventing a gastrointestinal disorder, a central nervous system disorder, an inflammatory disease, asthma, pain, migraine or emesis in a mammalian subject, which comprises administering to the said subject a therapeutically effective amount of a compound of claim 1.

6. A pharmaceutical composition for antagonizing substance P in a mammalian subject which comprises a therapeutically effective amount of a compound of claim 1 together with a pharmaceutically acceptable carrier.

7. A pharmaceutical composition for treating or preventing a gastrointestinal disorder, a central nervous system disorder, an inflammatory disease, asthma, pain, migraine or emesis in a mammalian subject which comprises a therapeutically effective amount of a compound of claim 1 together with a pharmaceutically acceptable carrier.

* * * * *